United States Patent
Lenardi et al.

(10) Patent No.: US 9,574,172 B2
(45) Date of Patent: Feb. 21, 2017

(54) METHOD FOR PRODUCING THREE-DIMENSIONAL MONOLITHIC MICROFLUIDIC DEVICES

(75) Inventors: Cristina Lenardi, Casciago (IT); Alessandro Tocchio, Arese (IT); Federico Martello, Parabiago (IT)

(73) Assignee: TENSIVE S.R.L., Milan (IT)

( * ) Notice: Subject to any disclaimer, the term of this patent is extended or adjusted under 35 U.S.C. 154(b) by 469 days.

(21) Appl. No.: 14/123,315

(22) PCT Filed: May 31, 2012

(86) PCT No.: PCT/IB2012/052732
§ 371 (c)(1),
(2), (4) Date: Dec. 2, 2013

(87) PCT Pub. No.: WO2012/164512
PCT Pub. Date: Dec. 6, 2012

(65) Prior Publication Data
US 2014/0106454 A1    Apr. 17, 2014

(30) Foreign Application Priority Data

May 31, 2011  (IT) .............................. MI2011A0995

(51) Int. Cl.
*C12N 5/00*   (2006.01)
*G03F 7/00*   (2006.01)
(Continued)

(52) U.S. Cl.
CPC ............ *C12N 5/0068* (2013.01); *B29C 45/00* (2013.01); *B81C 1/00523* (2013.01); *B82Y 10/00* (2013.01);
(Continued)

(58) Field of Classification Search
CPC ............ C12N 5/0068; B29C 2043/025; B29C 2045/0094; B29C 66/0042; B29C 2045/1702; B29C 2043/3668; B29C 70/546; B29C 70/547
See application file for complete search history.

(56) References Cited

U.S. PATENT DOCUMENTS 6,321,791 B1   11/2001   Chow
6,753,200 B2    6/2004   Craighead et al.
(Continued)

FOREIGN PATENT DOCUMENTS

DE   102009044645 A1   5/2011
EP       1614467 A2   11/2006
(Continued)

OTHER PUBLICATIONS

C. White, et al., "Synthesis and Characterization of Photodefinable Polycarbonates for Use as Sacrificial Materials in the Fabrication of Microfluidic Devices," Proceedings of the SPIE, The International Society for Optical Engineering SPIE, USA, vol. 4690, pp. 242-253 (2002).
(Continued)

*Primary Examiner* — Stella Yi
(74) *Attorney, Agent, or Firm* — Abelman, Frayne & Schwab

(57) ABSTRACT

A method is described for producing a microfluidic device (19), which comprises the phases of producing a three-dimensional template (15) of geometry equal to the channelings that is desired to obtain in the device; inserting the template in the desired position into a mold (16), keeping it suspended by at least one of its end; coating said template by immersion in (or deposition of) a material in the liquid phase (or dissolved or dispersed in a solvent) capable of solidifying by means of a chemical reaction or physical transformation, forming a material constituting the body of the final device; and selectively removing the three-dimensional template. In a variant of the method, useful for the production (Continued)

of scaffolds to be inserted into the human body, a porogenic material is added to the liquid precursor or to the precursor solution, such that the material of the solid matrix is characterized by a continuous structure of pores into which it is possible to insert live cells.

16 Claims, 13 Drawing Sheets

(51) Int. Cl.
*B29C 45/00* (2006.01)
*B81C 1/00* (2006.01)
*B82Y 10/00* (2011.01)
*B82Y 40/00* (2011.01)

(52) U.S. Cl.
CPC ............ *B82Y 40/00* (2013.01); *G03F 7/0002* (2013.01); *G03F 7/0017* (2013.01)

(56) References Cited

U.S. PATENT DOCUMENTS

| | | |
|---|---|---|
| 2002/0081787 A1 | 6/2002 | Kohl et al. |
| 2003/0012866 A1 | 1/2003 | Harnett et al. |
| 2003/0087198 A1 | 5/2003 | Dharmatilleke et al. |
| 2005/0170670 A1 | 8/2005 | King et al. |
| 2006/0014271 A1 | 1/2006 | Song et al. |
| 2007/0012891 A1 | 1/2007 | Maltezos et al. |
| 2009/0281250 A1* | 11/2009 | DeSimone ............ C08G 59/30 525/418 |

FOREIGN PATENT DOCUMENTS

| | | |
|---|---|---|
| WO | 0042233 A1 | 7/2000 |
| WO | 2004042797 A2 | 5/2004 |
| WO | 2005084191 A2 | 9/2005 |
| WO | 2006113492 A2 | 10/2006 |
| WO | 2009121037 A2 | 1/2009 |
| WO | 2010009320 A1 | 1/2010 |
| WO | 2011064716 A2 | 6/2011 |

OTHER PUBLICATIONS

C. White, et al., "Microsystems Manufacturing via Embossing of PHotodefinable Thermally Sacrificial Materials," Proceed of SPIE; Emergin Lithography Technologies VIII, vol. 5374, pp. 361-370 (2004).
International Search Report for PCT/IB2012/052732 mailed Aug. 9, 2012 (4 pages).
Written Opinion of the International Searching Authority for PCT/IB2012/052732 dated Aug. 9, 2012 (5 pages).

* cited by examiner

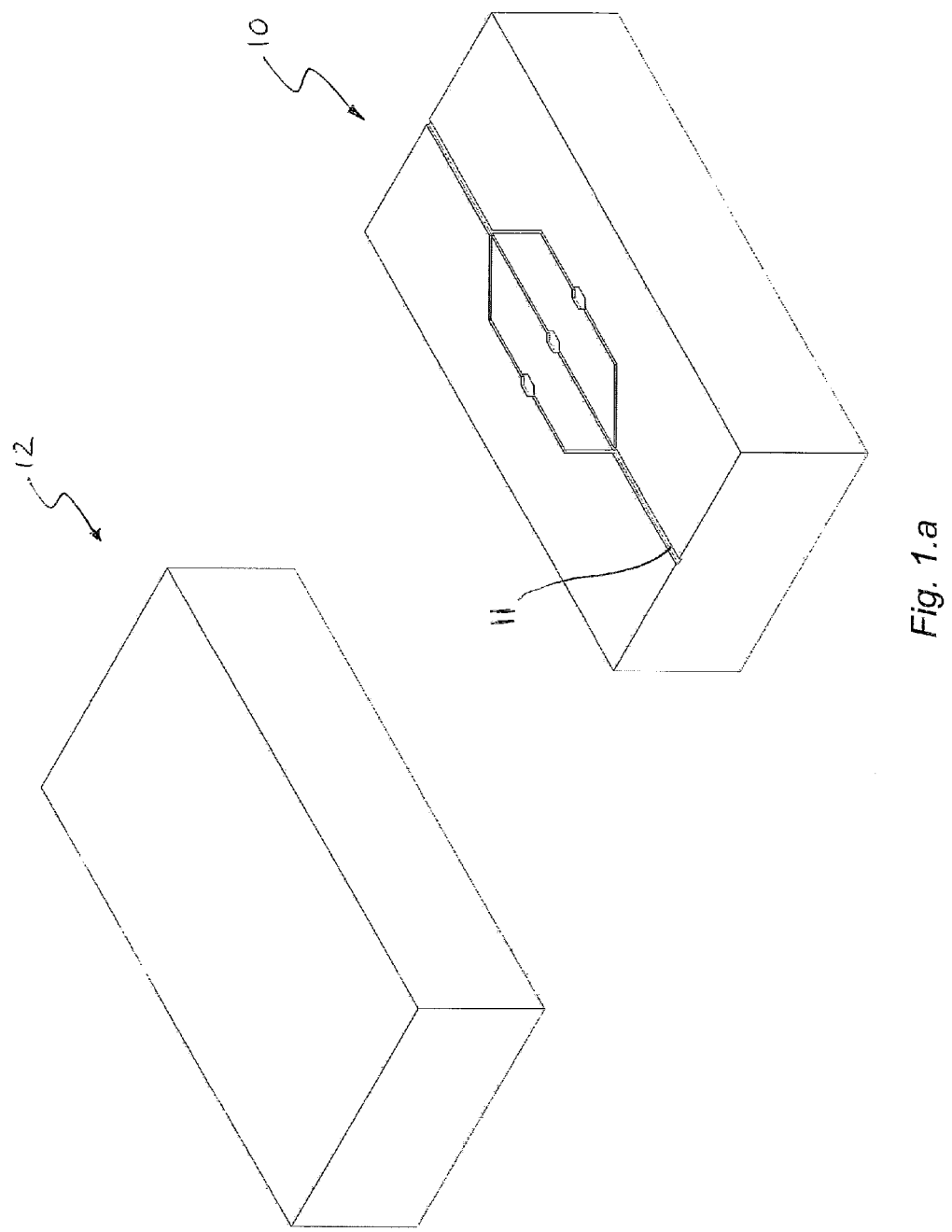

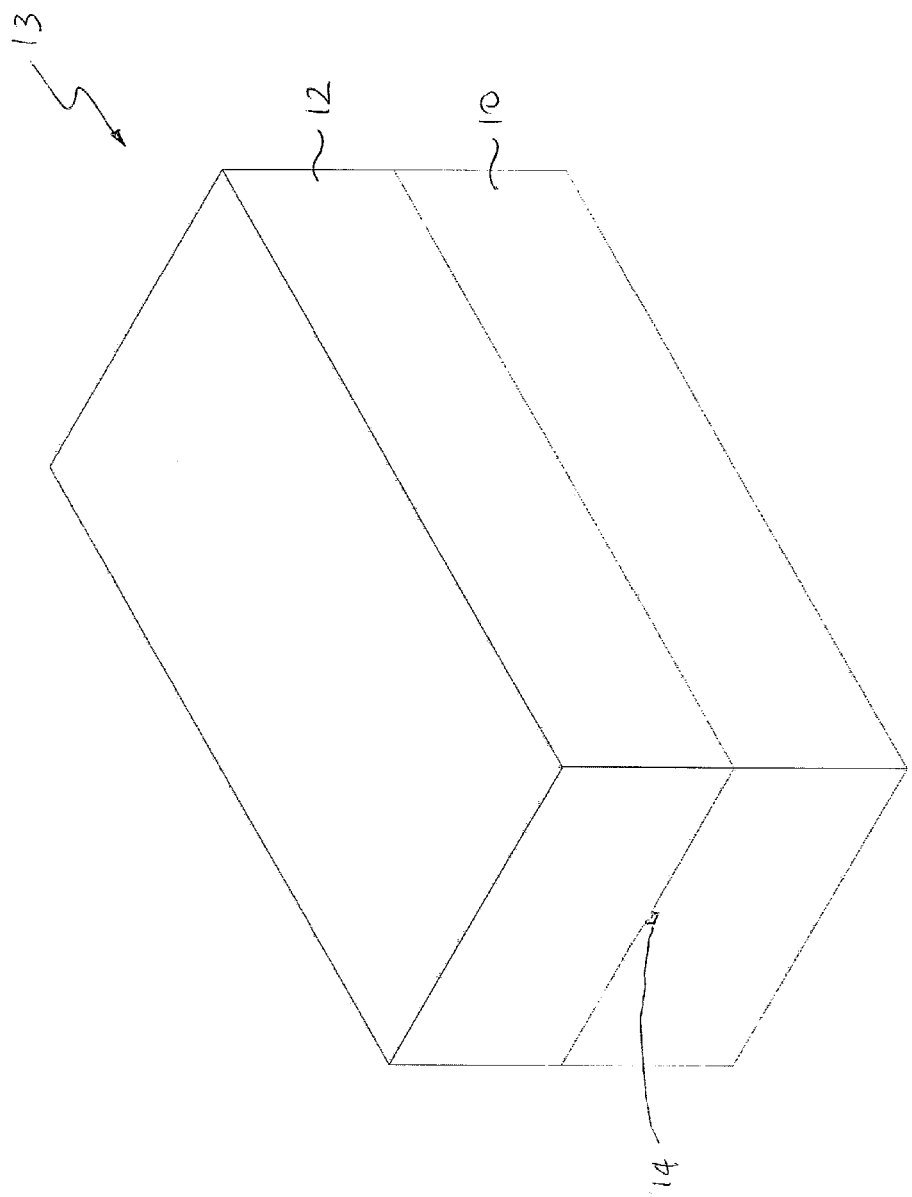
Fig. 1.b

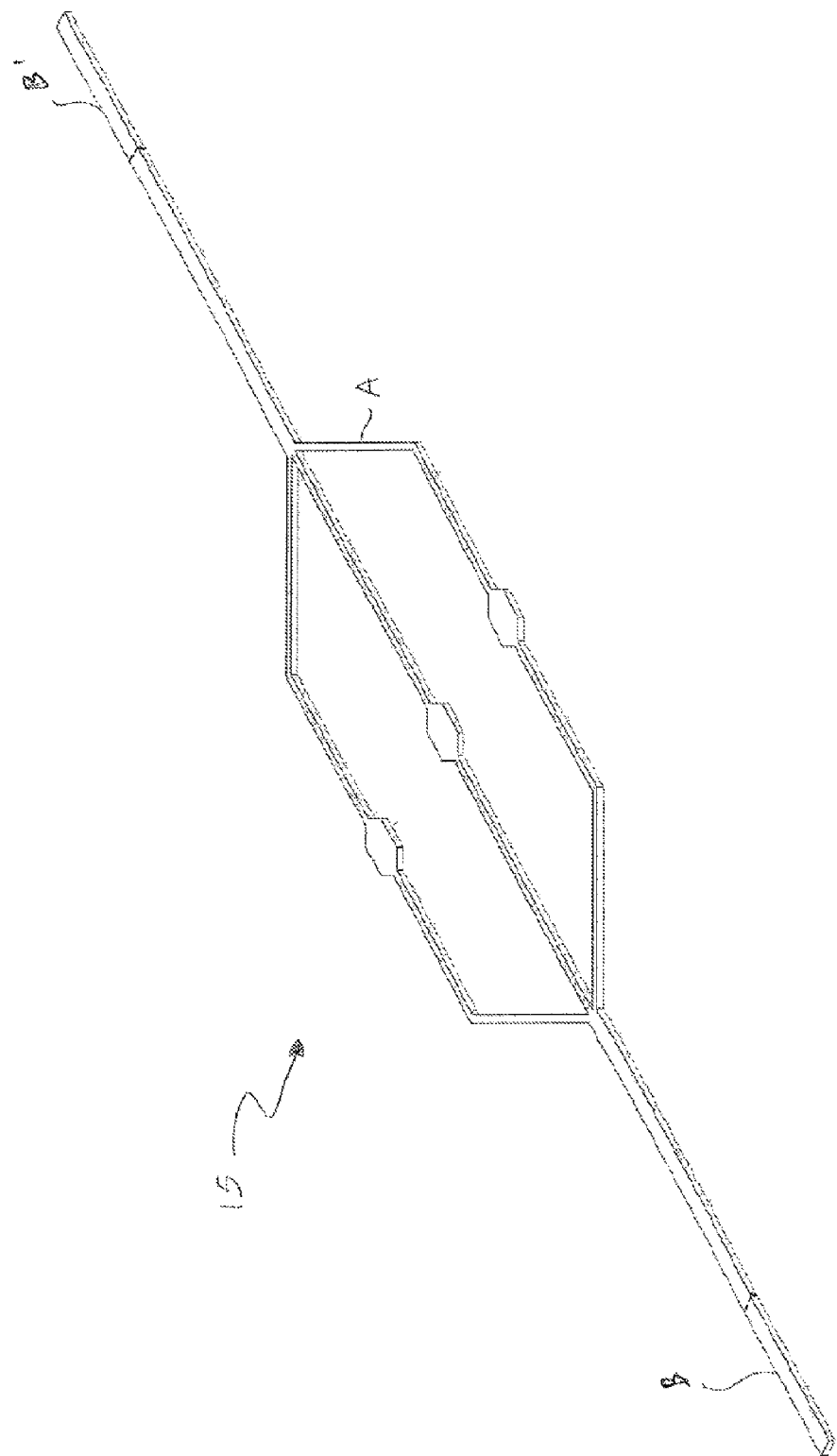
Fig. 1.c

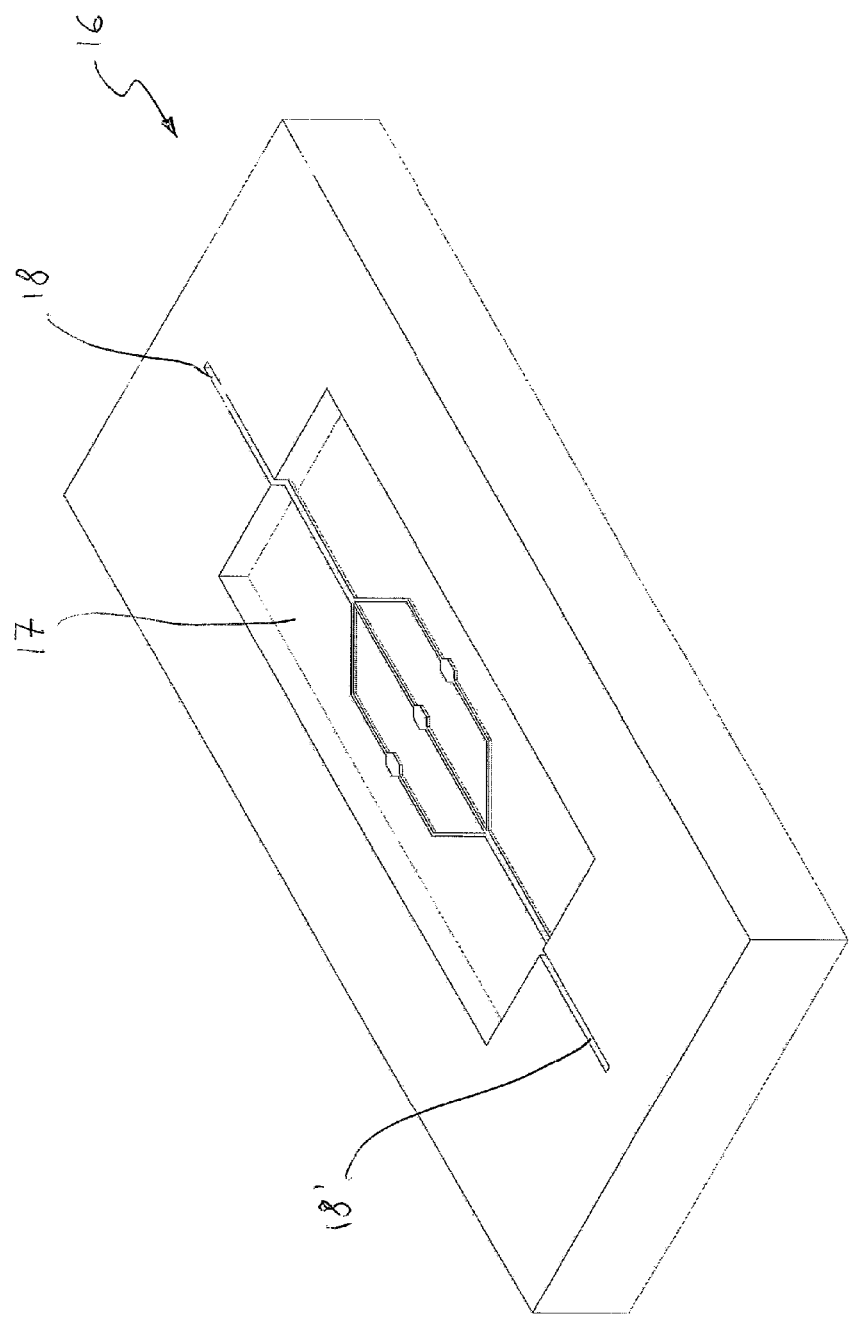
Fig. 1.d

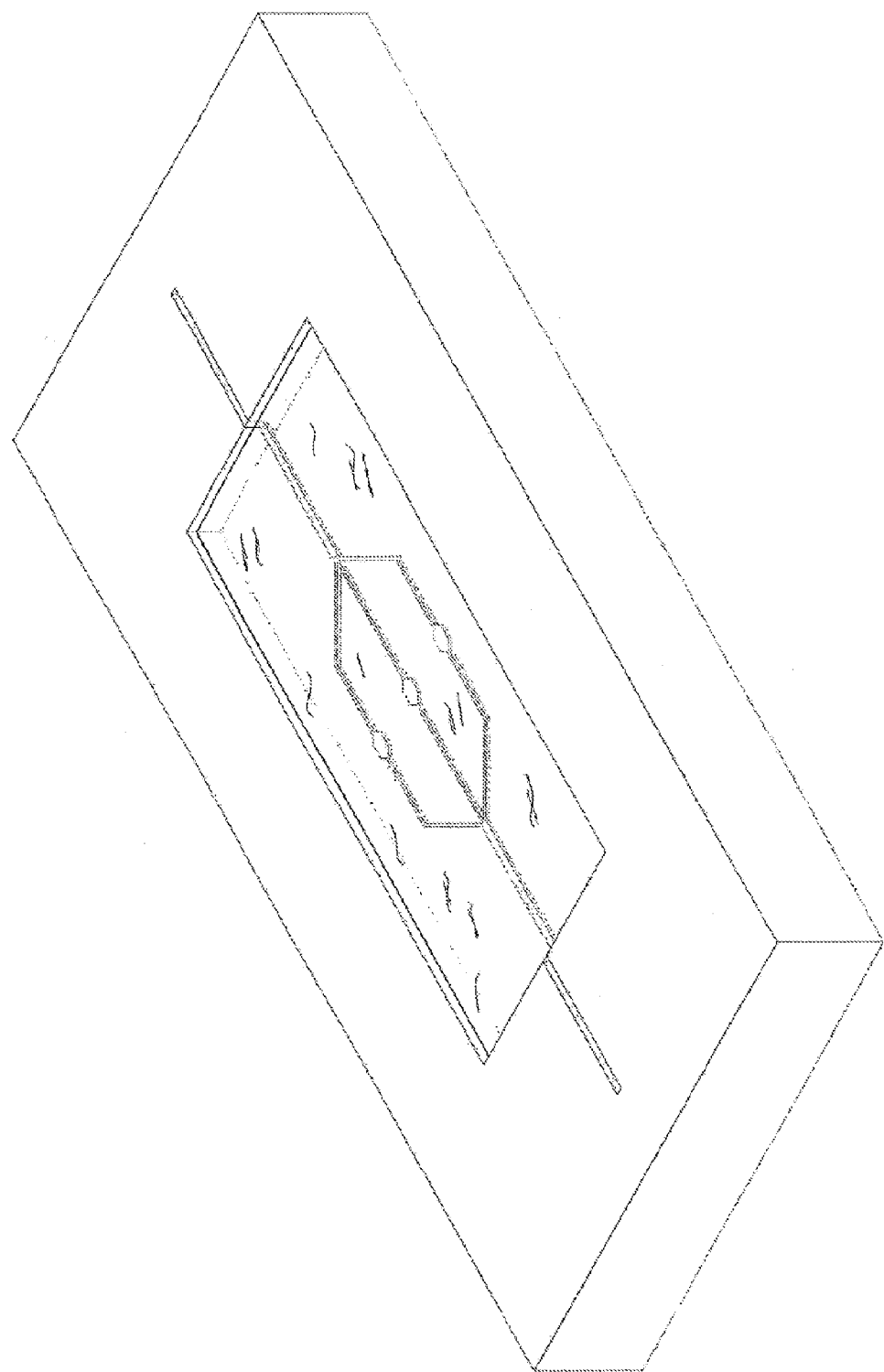
Fig. 1.e

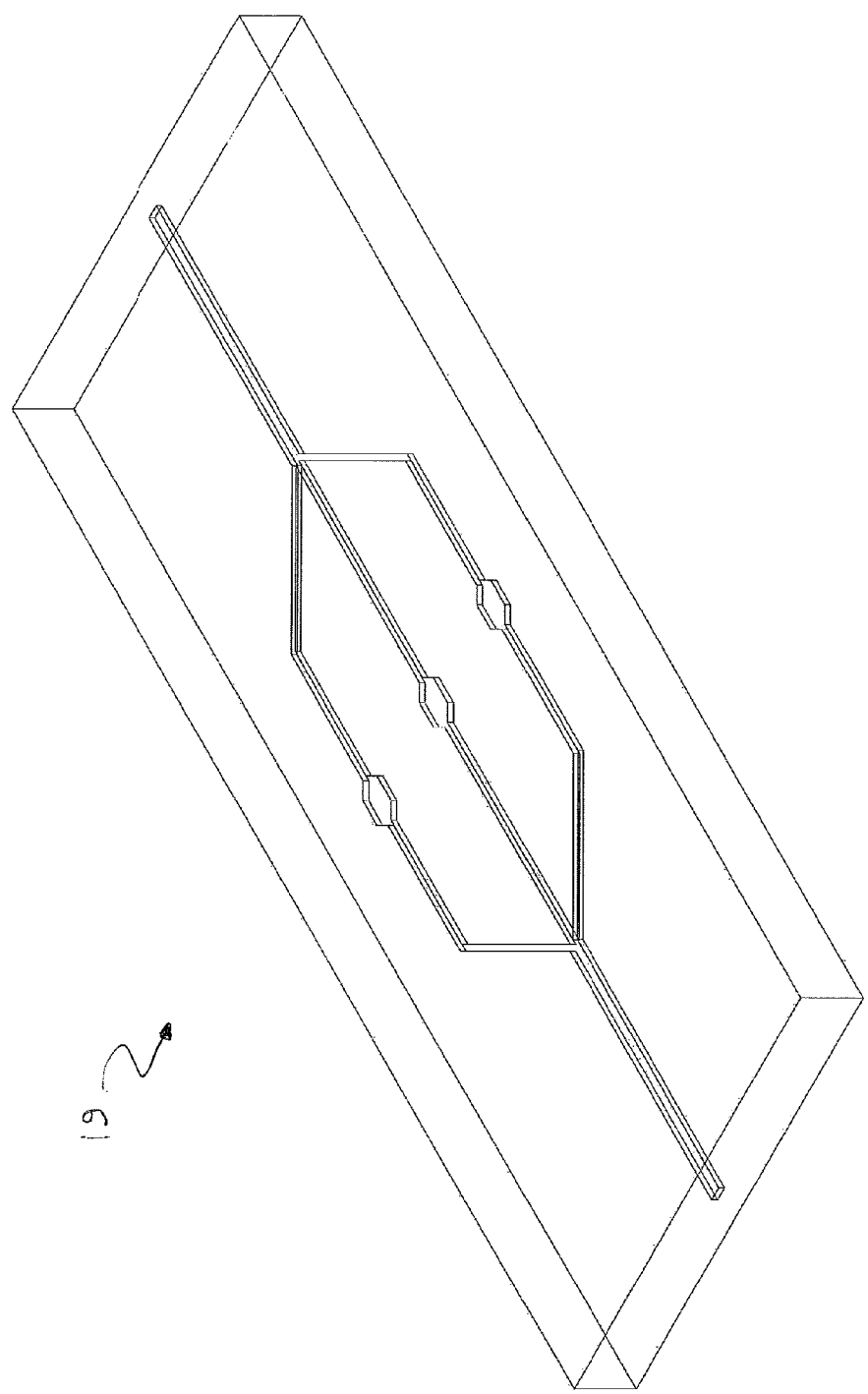
Fig. 1.f

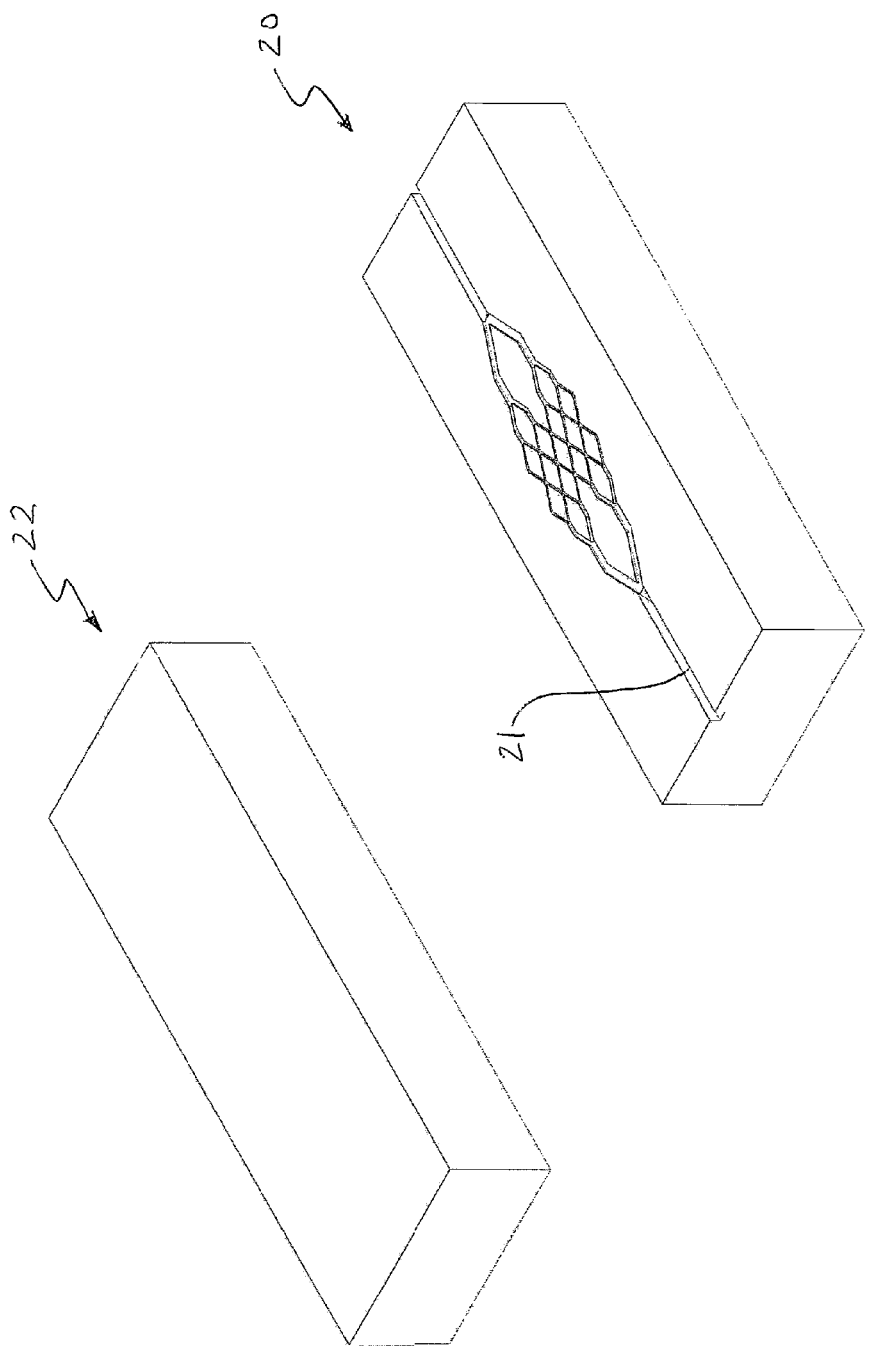
Fig. 2.a

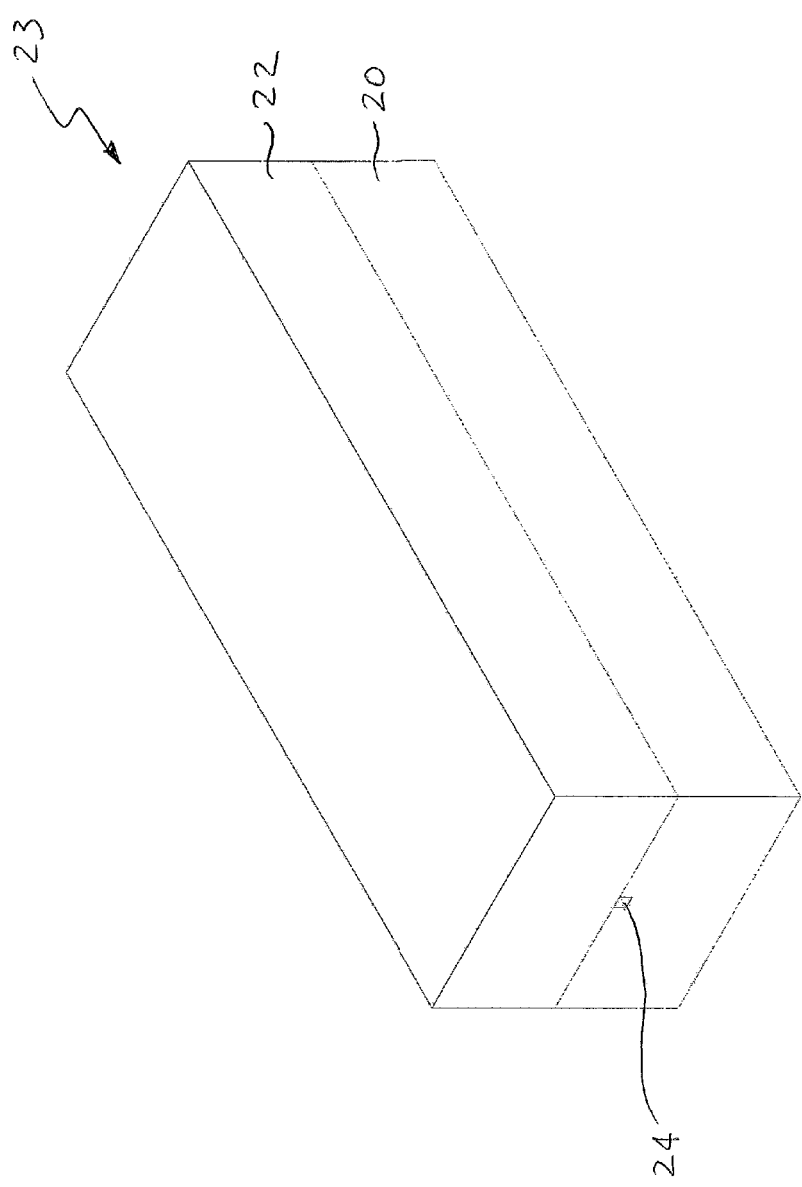
Fig. 2.b

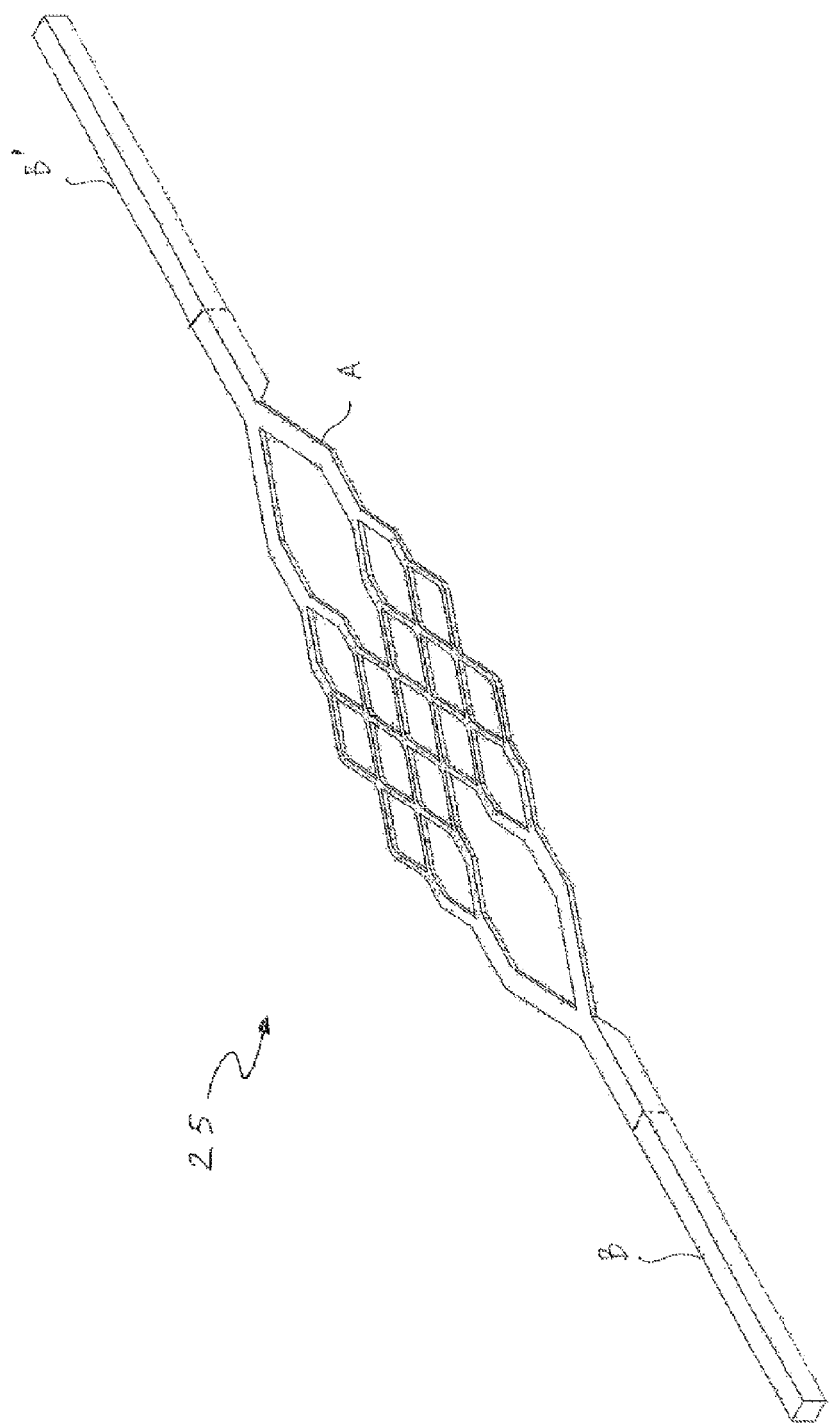
Fig. 2.c

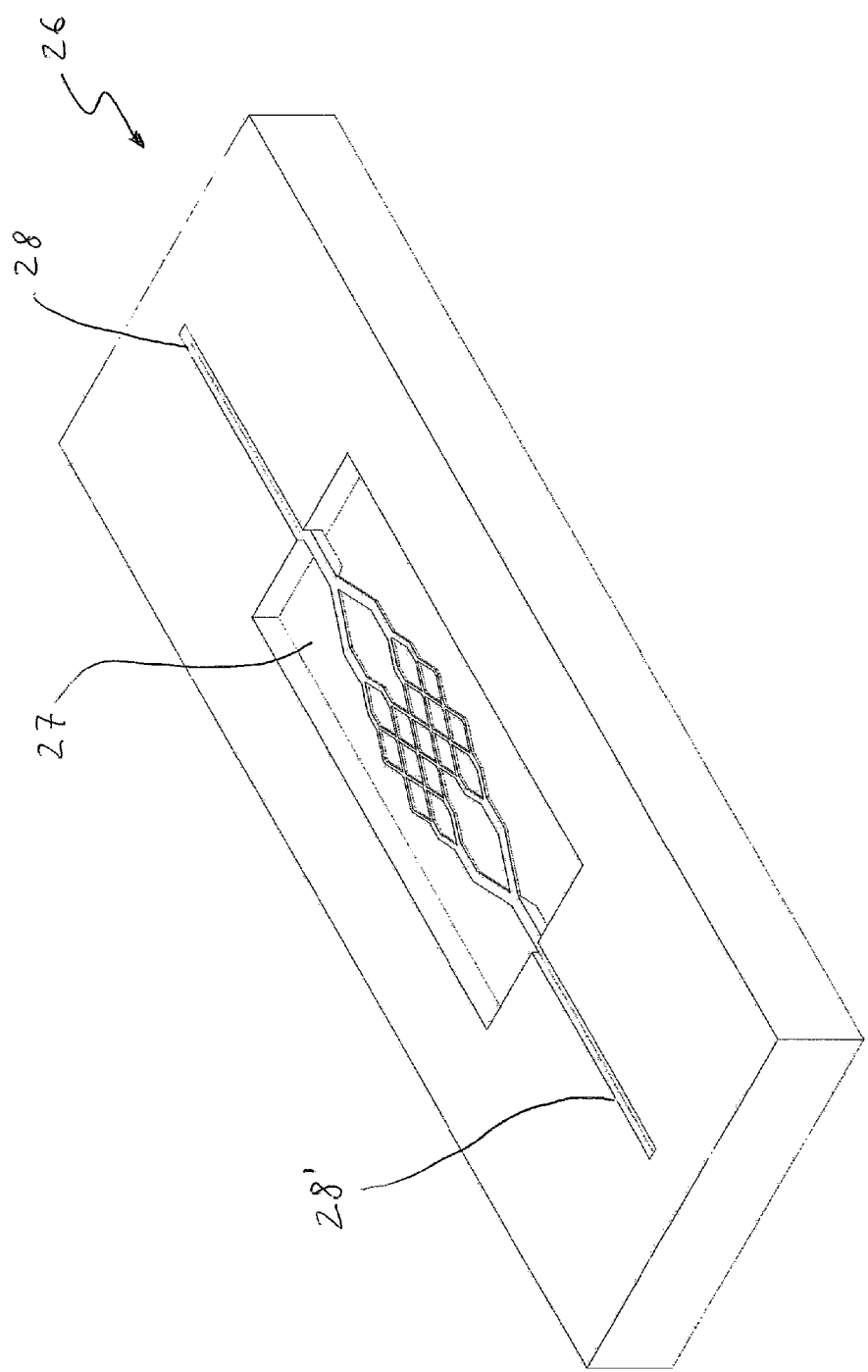
Fig. 2.d

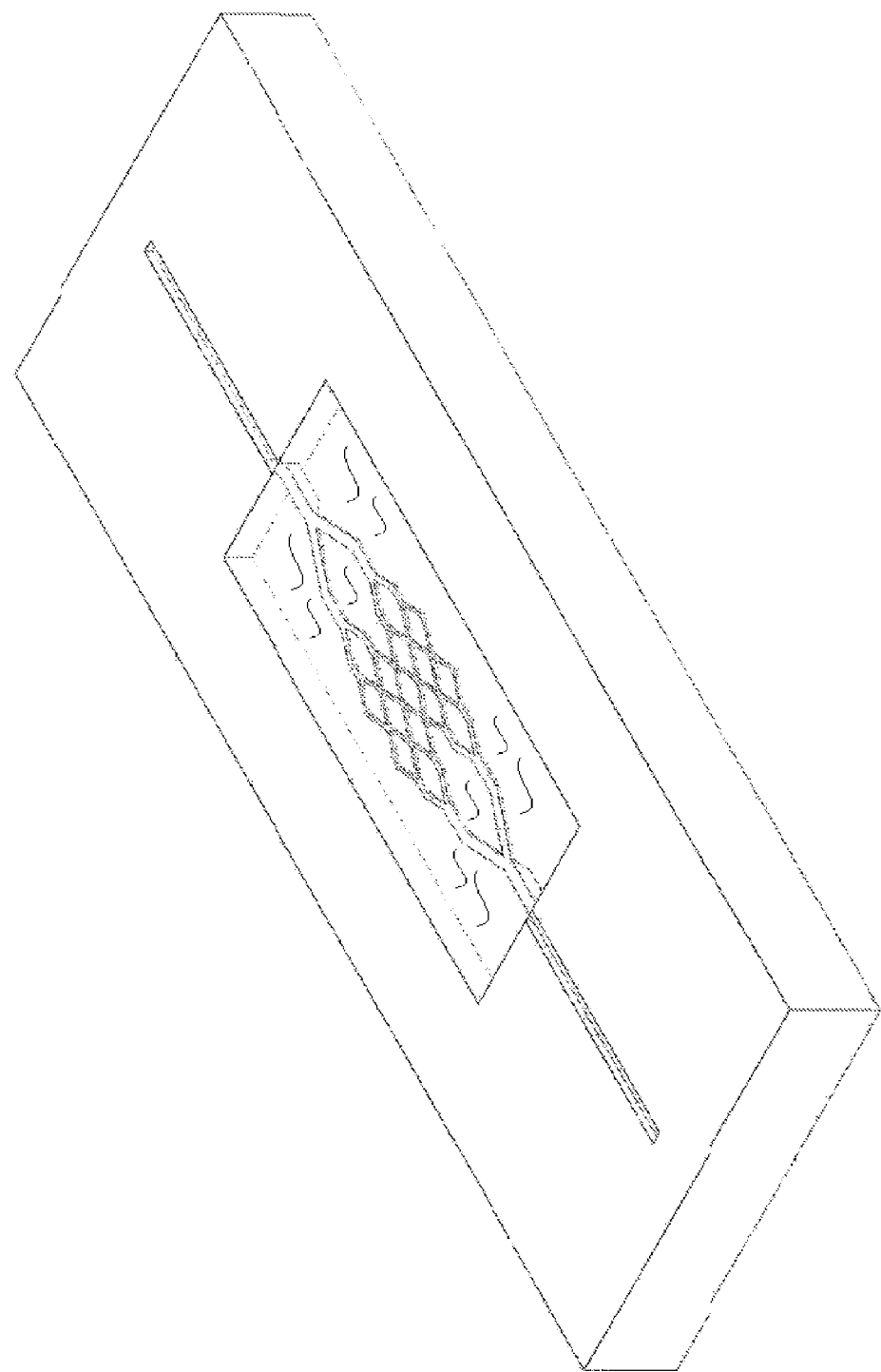
Fig. 2.e

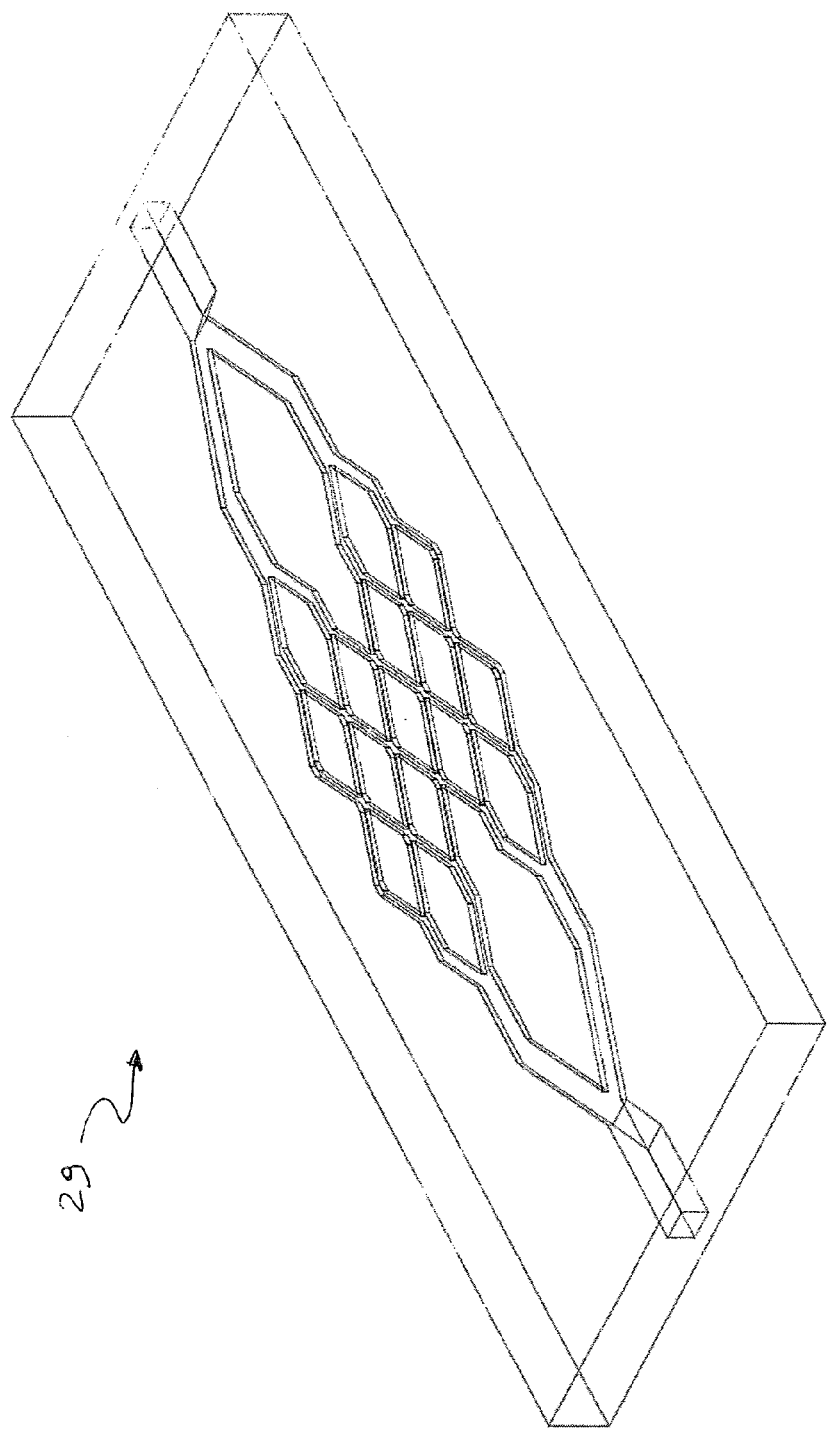
Fig. 2.f

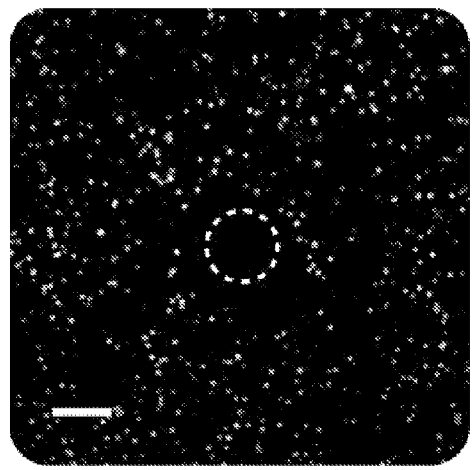 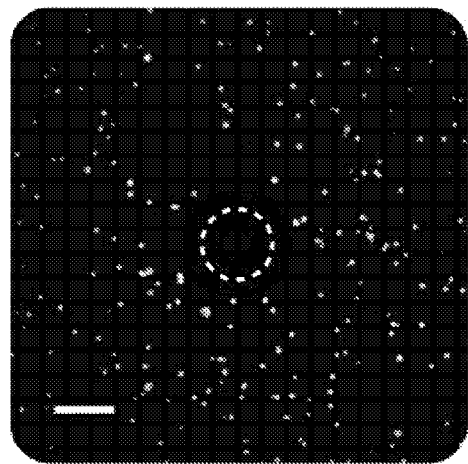
3.a 3.b
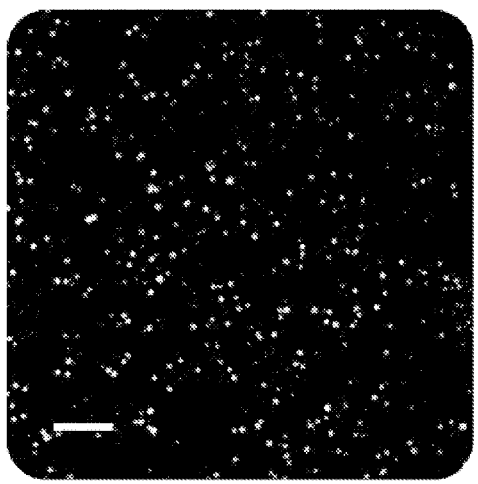 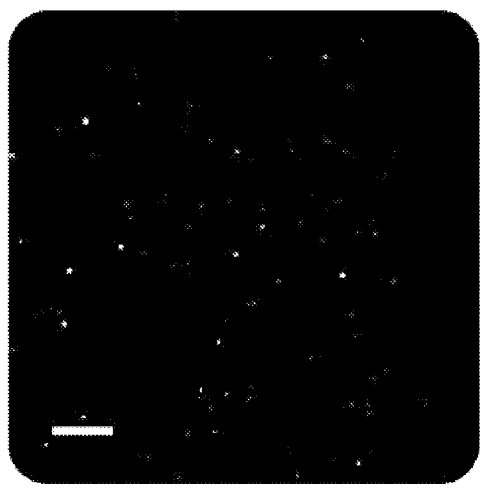
3.c 3.d
*Fig. 3*

METHOD FOR PRODUCING THREE-DIMENSIONAL MONOLITHIC MICROFLUIDIC DEVICES

RELATED APPLICATIONS

This application is a U.S. national phase application under 35 USC §371 of PCT/IB2012/052732 filed on May 31, 2012, and claims the benefit under 35 USC §119 of Italian patent application number MI2011A000995 filed on May 31, 2011, the disclosures of which are incorporated herein by reference in their entireties.

FIELD OF THE INVENTION

The present invention relates to a method for the manufacture of three-dimensional monolithic microfluidic devices.

PRIOR ART

Microfluidic devices are manufactured articles commonly produced from glass, silicon or polymeric materials containing channelling which extends in two dimensions (i.e. substantially in one plane within the device) or in three dimensions, within which fluids may be caused to flow. The devices generally have dimensions of up to a few centimeters, whereas the channels have cross sections with sides (or diameter, in the case of canals of circular cross-section) generally from tens to hundreds of micrometers (μm) in size; in the broader meaning of the term, microfluidic devices may also include those systems in which the channels have cross sections of the order of a few millimeters; in the remainder of the text and in the claims, the definition "microfluidic devices" will be used in the sense of this latter, broader meaning.

Microfluidic devices have a variety of possible applications: for example, with appropriate functionalisations of the channel walls, they can act as detectors of the presence of one or more analytes in a fluid (thus functioning as active elements of miniaturised analysers, also known in the field by the English definition "Lab on a chip"), particularly in applications in the biological and medical field, or as chemical microreactors. The use of these systems in the biological field has increased in recent years, especially with regard to applications in microscopy, culturing, cell counting and cellular manipulation, and high-throughput experiments. One extremely important advantage of these devices is that their functioning requires minimal quantities of fluids as compared with conventional systems, and consequently the use of minimal quantities of (frequently expensive) reagents, as well as reducing the volumes of liquid to be disposed of, for which special procedures are normally required.

In one particularly interesting variant, if made of biocompatible materials these manufactured articles can be used in the production of vascularised prostheses, and if said materials also have the characteristic of being biodegradable or bioabsorbable in a suitable time span, these prostheses can function as sites of tissue regrowth, which are then replaced with naturally produced tissue (so-called "scaffolds").

Given the number and the importance of the possible areas of use, in recent years a considerable volume of research and development work has been carried out in the field, focused on the production and perfection of microfluidic devices having desired characteristics.

The first devices of this type were produced using methods and materials derived from the field of semiconductors and microactuators (better known as "micromachines" in the sector), with sequences of selective deposition and/or removal of portions of deposited layers; examples of these methods are described in patent applications EP 1614467 A2, US 2002/0081787 A1, US 2003/0012866 A1, US 2005/0170670 A1, US 2006/0014271 A1, WO 00/42233 A1, WO 2004/042797 A2, WO 2006/113492 A2, WO 2011/064716 A2, in U.S. Pat. No. 6,753,200 B2 and in the articles "Synthesis and characterization of photodefinable polycarbonates for use as sacrificial materials in the fabrication of microfluidic devices", C. White et al., proceedings di SPIE, vol. 4690 (2002), pages 242-253, and "Microsystems manufacturing via embossing of photodefinable thermally sacrificial materials", C. White et al., SPIE proceedings, vol. 5374 (2004), pages 361-370. The principal limiting factor in these methods is that they are only able to produce two-dimensional structures on a substrate, in which the channelling in practice extends only in one plane within the manufactured article, thus yielding relatively simple devices, also due to the impossibility to superimpose or cross over two or more channels; at most, the documents cited above describe the possibility of producing devices with channelling on more than one parallel plane by applying the planar channelling-production methods several times in succession, and interconnecting channels on different planes by means of apertures perpendicular to the planes themselves. Analogous results have been obtained using the pressing methods described in patent applications WO 2005/084191 A2 and US 2007/0110962 A1.

U.S. Pat. No. 6,321,791 and patent application WO 2009/121037 A2 relate to devices in which the channels, although three-dimensional, are obtained by superimposing several two-dimensional channelled structures which lie in mutually parallel planes, and by interconnecting said structures by means of apertures perpendicular to said planes. In these devices, the different levels may be obtained by successive superimpositions, or by constructing them separately and then joining them mechanically or by adhesion. In the first case, the process for producing a multiplanar structure is lengthy and laborious; in the second case, the devices obtained are not monolithic, and there may be imperfections of contact or adhesion between the surfaces of two adjacent layers, leading to problems in the use of the device; for example, a fluid could diffuse from a channel into interstices between two adjacent layers, causing contamination and/or malfunction of the device.

Other documents propose an alternative approach to the production of microfluidic devices. According to this route, three-dimensional structures (also referred to as "3D" below) are produced with a sacrificial material, which can be dissolved as a result of appropriate treatments; the structure (negatively) corresponds to the extension of the channels that are to be formed within the final device; this structure is inserted into a mould into which a liquid material is then poured, which material may then solidify (or be solidified); at the end of the process, the initial 3D structure is removed by chemical attack or by heating (or both), leaving spaces and empty channels in its place.

This method is used, for example, in patent application US 2003/0087198 A1. According to this document, the sacrificial 3D structure is made out of wax, by "drawing" filaments from a bath of molten wax through a solid "seed" of the same material (method analogous to Czochralski's method for growing monocrystals of pure silicon); the filaments thus obtained can then be fashioned or interconnected to obtain the desired 3D structures. In the text of the application, it is stated that the cross-section of the wax thread obtained (which will correspond to the cross-section of the channels in the final device) can be controlled by acting on parameters such as, inter alia, the temperatures of the melt and of the external environment, the viscosity of the molten wax, the diameter of the cold "seed" and the rate of raising thereof. This system has the drawback of being complicated to implement in practice, so that the production of each individual sacrificial structure takes a long time; the method of this patent application may therefore be suitable for feasibility studies on the laboratory scale, but on the whole it cannot be used in large-scale industrial production.

Patent application US 2007/0012891 A1 describes a system analogous to the previous one, but in which the sacrificial 3D structure is obtained by working from the solid material, with equipment used for the production of prototypes (it is exemplified the Solidscape T66 instrument) in sectors such as jewellery, modelling, or in the production of masters by post-fusion mechanics. In this case too, the limit of the method consists in the fact that sacrificial structures must be produced one by one by precision machining, leading to long times (and therefore high costs) of production, that are incompatible with industrial applications Finally, patent application WO 2010/009320 A1 describes a method that is especially suitable for the production of channelled structures that are to be used as "scaffolds" for use in regenerative medicine. According to the method of this document, a filamentous mass of elongate fibres is produced from a sacrificial material by extrusion, or by using various techniques that are well known in the production of polymeric fibres, which come under the general definition of "spinning" (methods cited are melt-spinning, wet-spinning, dry-spinning, dry-jet wet-spinning and electro-spinning); the mass is then collected with, or on, one or more supports of elongate form, substantially long sticks or tubes manufactured in their turn from a sacrificial material, in a way overall analogous to the preparation of spun sugar (sugar is in fact the preferred sacrificial material indicated in this document); the assembly thus obtained is then used as a 3D sacrificial structure in the way described with reference to the preceding documents. This method is limited above all in that the structure of the channels corresponding to the fibres is entirely random and therefore the reproducibility of the results cannot be successfully controlled; in the second place fibres obtained are very thin and, in some cases, they may not have sufficient characteristics as to consistency and dimensional stability, and may fold and collapse under the weight of the liquid material with which they are submerged in the mould, before the latter solidifies.

SUMMARY OF THE INVENTION

The aim of the present invention is to provide a simple method for the production of monolithic three-dimensional microfluidic devices which overcomes the problems of the prior art, as well as to provide the manufactured articles obtained by means of said method.

These aims are achieved according to the present invention which, in a first aspect thereof, consists in a method for the production of a monolithic three-dimensional microfluidic device, comprising the following steps:

producing, with a sacrificial material, a three-dimensional template of stable form, consisting of a part, A, corresponding to the channelling of the microfluidic device, and one or more parts B, B', ..., not corresponding to said channelling;

positioning said three-dimensional template into a mould, by suspending it from at least one of said parts B, B', ...;

covering said three-dimensional template, leaving out said parts B, B' ..., with a precursor, liquid or in solution, of a solid matrix, said precursor being able to solidify by chemical reaction or physical transformation forming a matrix making up the body of the final device;

causing the solidification of said precursor;

selectively removing the sacrificial material by a heat treatment and/or by dissolution with a solvent thereof.

The terms used in the definition of the invention given above, as well as in the remainder of the text and in the claims, must be understood in their ordinary sense unless otherwise specified. Specific definitions of some of the terms used in the present description are given below:

in the present description, for the sake of brevity reference is made to a sacrificial material and to a precursor, but by these definitions mixtures of sacrificial materials and precursor materials are also intended;

the final structure of the device, obtained following the removal of the sacrificial material, will be indicated with "matrix", and the material obtained by solidification of the precursor (or precursors mixture) will be indicated as "material of the matrix";

"three-dimensional template of stable form" means a structure capable of keeping its shape when subjected uniquely to the force consisting of its own weight, in air or when immersed in the liquid precursor or in solution, but deformable in consequence of the application of mechanical forces (for example traction, compression or torsion); for brevity, this member will, in what follows, also be referred to simply as a template.

BRIEF DESCRIPTION OF THE DRAWINGS

The invention will be illustrated in detail below with reference to the drawings, wherein:

FIG. 1a-f represent, in diagrammatical form, the sequence of steps of the method of the invention directed to the production of a first microfluidic device;

FIG. 2a-f, analogous to FIG. 1 a-f, represent the sequence of steps for producing a second microfluidic device, with channels and micro-wells for cellular cultures; and FIG. 3a-d depict fluorescence images which show live cells in a vascularised device according to a preferred embodiment of the invention and in an analogous device according to the prior art.

DETAILED DESCRIPTION OF THE INVENTION

The template used for producing microfluidic devices according to the invention may be produced in one piece but, in particular for the realisation of complex geometries, may also derive from the union of a plurality of parts; in the remainder of the description, reference is predominantly made to the case of the single-piece template, but all the teachings reported in what follows also apply to the case in which a plurality of 3-D structures are interconnected to form the final template.

The first step of the method of the invention consists in obtaining the template, which can be made from any sacrificial material that may be readily dissolved with a solvent or liquefied by heat treatment, without the solvent or the heat treatment damaging or altering the material of the matrix.

The sacrificial material may be selected, for example, from waxes or, preferably, thermoplastic polymers such as poly (methyl methacrylate) (PMMA), polyvinyl alcohol (PVA), polycarbonate (PC) and polystyrene (PS); because the thermoplastic polymers are the preferred materials for realising the invention, reference will be made thereto in the remainder of the description, but it remains understood that the invention may also be realised with sacrificial materials of other type.

The step of producing the template may be performed using any known method for making parts from thermoplastic materials. The template is preferably produced using a technique selected from casting, hot injection into a mould, hot-pressing, thermoforming and laser cutting.

The casting method consists of pouring into an open mould a polymer, molten or dissolved in a suitable solvent, or a liquid precursor thereof; leaving the polymer to solidify; and extracting the formed part from the mould, obtaining a three-dimensional structure which is a replica of the cavity of the mould. In case of a polymer being used, this is generally poured into the mould in the molten state, i.e. it is brought to a temperature greater than the melting point, poured into the mould and allowed to cool to a temperature below the melting point; the polymer is preferably solid at ambient temperature, so that cooling systems for its solidification are not necessary. In the case in which a polymer precursor is used, the precursor (for example, oligomers thereof) is poured into the mould, and its reticulation is effected by known methods, for example by heating, by irradiation with UV or with radical reaction initiators. In order to obtain three-dimensional structures of the desired shape, the top surface of the mould containing the molten polymer or its precursor may be "shaved" to remove all the excess polymer or precursor; at the end of the process, any burrs (thin skins of polymer connected to the desired structure) can be removed by mechanical methods or by chemical attack (because the rate of chemical attack is constant on all parts, the thinnest ones are removed when the principal structure of the template is still essentially unaltered).

In the hot injection method, the thermoplastic material in the molten state is forced under pressure to enter the cavity of a mould, called the "master", which is composed of two or more separate parts mechanically held together during the injection, for example with screws, clamps or the like. The position and dimensions of the channels or of the other empty spaces in the master exactly replicate those of the final microfluidic device or of one of its parts. The various parts of the master can be produced using known micro-manufacturing methods, which enable details of the order of 100 μm and even less in size to be reproduced. The individual parts constituting the master generally have the form of low parallelipeds, and are stacked by placing their largest surfaces in contact. The canals and other empty spaces of the master can be in the form of recesses of appropriate geometry on one of the larger surfaces of one or more parts, in such a way that a second part of which the master is comprised, joined to the one presenting the recesses, defines channels or other empty spaces of generic shape. The parts of the master may then present channels in a direction perpendicular to the larger surfaces of the part; in this way communication passages are created between different levels of the assembly of channels and empty spaces, or with the outside of the master. In the case of masters produced from a plurality of parts, the canals perpendicular to the larger surfaces may also be obtained by dividing one or more of these parts into two sub-parts, presenting the latter within the assembled master along two faces perpendicular to the larger surfaces, and having formed recesses in at least one these faces. Once the master has been assembled, the sacrificial material is injected into the interior thereof under pressure and in the molten state; under these conditions, the molten thermoplastic polymer occupies all the empty spaces within the master. After solidification of the melt, it is possible to disassemble the master and extract a 3D structure (that is, the template) of geometry equivalent to the desired network of channels and empty spaces within the final microfluidic device. Alternatively, as said above, the structure obtained in this way can be equivalent to only one part of the desired template; in this case the complete template is obtained by joining two or more 3-D structures, for example by causing them to adhere by heating.

An example of application of the hot injection method to the production of two possible 3D structures is shown in FIGS. 1.a, 1.b and 2.a, 2.b. FIG. 1.a shows two parts 10 and 12 of parallelipipedal shape which are intended to be combined with one another to form the master as described above; on one surface of the part 10, a network of channels and interconnected cavities is formed, overall indicated in the drawing as a member 11. The union of part 10 (in particular the surface thereof in which the network of channels 11 is present) with part 12 of forms the master, 13, shown in FIG. 1.b; the master has two apertures 14 (only one visible in the drawing) at the level of the end of the channel network 11. Analogously, FIG. 2.a shows the parts 20 and 22 (the former having a network of channels and cavities 21 which is more complex and articulated than network 11), which form the master 23 with apertures 24 of FIG. 2.b A template made of a thermoplastic material may also be obtained by hot-pressing (a method better known in the sector as "hot embossing", term which will be used below). This method consists in arranging a sheet of a thermoplastic material on a surface of one part of a mould, which may be completely planar or have a group of recesses corresponding to the desired structure; bringing the thermoplastic polymer to a temperature within the range between that of vitreous transition ($T_g$) and that of melting of the polymer itself, causing it to soften; and pressing the other part of the mould against the softened polymer. In case the first part already has recesses, the second one, which is pressed onto the melt, may be flat or in turn have recesses. After pressing, the thermoplastic material is allowed to cool to below its $T_g$, the two parts of the mould are separated, and it is then possible to extract the template from the mould. In this case, the structures obtained extend principally in two directions (corresponding to the planes which come into contact in the closed mould), with the possibility of having parts running in the third dimension, perpendicular to the first two, derived from bores which pass and are perpendicular to the larger surfaces of the two parts of the mould. Any pressing "burrs" may be eliminated simply by a procedure of chemical or physical attack (methods known generically by the name of "etching").

The template may also be obtained by means of the Injection Compression Molding process, which combines the advantages of the injection phase and of the subsequent compression phase, eliminating the drawbacks due to the long paths traveled by the thermoplastic material in the mould. In a first phase, a volume of dissolved polymer, corresponding to the volume of the part to be pressed, is injected into the mould, which remains partially open. Thanks to the larger space between the parts of the stamp, the injection is performed at low pressure, thus reducing the velocity and cutting force of the polymer. Following the injection phase, the two parts of the stamp our joined together during the compression phase. This phase is in its turn subdivided into controlled speed motion and finally, if the desired compression strength is reached, into maintenance of the final pressure at a controlled force during the cooling period.

Another possible method for producing the template is laser cutting. In this case, a sheet of the polymeric sacrificial material is provided and cut with the laser so as to obtain a two-dimensional structure of the desired shape.

The sacrificial material template may also be produced by other known methods, for example by thermoforming, as will be evident to the experts in the field.

In the case of sacrificial templates obtained by hot embossing or laser cutting, complex 3D structure can be obtained by simple joining (for example, by localised melting) of two or more primary structures, as described in relation to hot injection. Alternatively, it is possible to deform substantially two-dimensional (2D) sacrificial structures by exploiting the elasticity of thermoplastic materials so as to achieve 3D development of the structure; this latter method may also be used together with that of joining a plurality of initially substantially 2D structures.

In one variant of the method invention, the template may be completely or partially covered with a material having a desired functionality (provided said material is capable of resisting the subsequent treatments of production of the microfluidic device). For example, it is possible to cover the surface of the template with a metallic powder, by immersing it in hot metallic powders, which cause the localised fusion of the thermoplastic material and the incorporation of a layer of powder on the surface thereof after cooling. Alternatively, it is possible to implant particles onto surfaces of the template in accordance with the techniques described in the articles "Micro- and nanoscale modification of poly (2-hydroxyethyl methacrylate) hydrogels by AFM lithography and nanoparticle incorporation", A. Podedstà et al, Journal of Nanoscience of Nanotechnology, 5(3), 425-430, 2005, and "Poly(methyl methacrylate)-palladium clusters nanocomposite formation by supersonic cluster beam deposition: a method for microstructured metallization of polymer surfaces", L. Ravagnan et al., Journal of Physics D: Applied Physics, 42(8), 082002/1-082002/5, 2009. The first one describes the production of a "bed" of nanoparticles of carbon on the internal surface of the mould into which the precursors of the studied polymer are then poured; particles of carbon are incorporated in the superficial layers of the polymer during the cross-linking thereof; the second one describes the application of a method for obtaining deposits of metallic nanoparticles (palladium in the case of the article) in a rigid polymer.

The template obtained according to any one of the methods described above have dimensions greater than the network of channels which is desired within the final microfluidic device. In particular, the template will be composed of a principal part of larger dimensions, A, corresponding to the channels of the final microfluidic device, and one or more parts, B, B', ... which have no correspondent in said channels. This condition is illustrated in FIGS. 1.c and 2.c with reference to the two three-dimensional templates of stable form, 15 and 25, which are obtained through the use of the masters 13 and 23 described above, but obviously the same condition is also required according to the invention for templates of other 3D shapes, or also obtained with any of the other methods mentioned above (not necessarily with recourse to the master). In FIGS. 1.c and 2.c, parts B and B' (shown separately from parts A of templates 15 and 25 by means of broken lines) are ends of the template that are used in the production procedure of the microfluidic device to hold the template itself in the desired position inside the mould in which the precursor of the matrix will be inserted.

The template thus obtained is then inserted into a mould. The template is held laterally by means of the parts B and B'. FIG. 1.d shows the manner of use of the template 15. The mould, 16, has a principal cavity 17 and two grooves 18 and 18', the depth of which is less than that of the cavity; the ends B and B' of the template 15 are supported in these grooves, allowing the template to be maintained in the desired position detached from the bottom of the cavity 17. Analogously, FIG. 2.d shows a mould 26 which has a cavity 27 and the grooves 28 and 28' into which are inserted the parts B and B' of template 25, maintaining it detached from the bottom of the cavity 27.

Into the cavity (17 or 27) of the mould a precursor, liquid or in solution, of a solid matrix is then poured, so as to completely cover the template contained into the cavity, as shown in FIGS. 1.e and 2.e; in FIG. 1.e, the precursor is poured up to the level shown by the solid line, and does not completely fill the cavity 17, whereas in FIG. 2.e, the precursor completely fills the cavity 27.

To avoid that the liquid precursor (or the solution containing it) also fills the part of the grooves 18, 18' and 28, 28' not occupied by parts B and B' the template, it is possible to introduce members (not shown in figures and generally made of the same material as the mould) into the grooves, which members have width equal to that of said grooves, placed in contact with the parts B and B' and in positions such as to close the entry to the grooves above the parts B and B'. Alternatively, it can be left that the precursor also occupies the grooves, and remove (for example, by cutting) the corresponding parts from the final microfluidic device. Even though the case of only two parts B and B' is shown in the drawings, which are supported on two sole grooves within the mould, which grooves are positioned at the same level, according to the invention the template can have a plurality of parts of type B and B', which result at different heights when the template is inserted into the cavity of the mould, thus giving place to a plurality of points of entry, at various heights, of the channels of the final microfluidic device.

The sacrificial material and the precursor must be selected so as to satisfy a number of conditions during the steps of carrying out the method.

The precursor must be capable of solidifying by means of chemical reaction or physical transformation, and said reaction or transformation must entail the use of chemical compounds, the adoption of physical conditions, and operational steps, such that the template remains substantially unaltered, or at least maintain its continuity, during the time necessary for solidification of the precursor; the definition "maintain continuity" referred to the template, indicates that, even if this can be partially dissolved at its surface, the dissolution must be of little entity, and such that the continuity of the template is not interrupted at any point.

This condition can be achieved most simply by selecting as the precursor a liquid chemical compound in which the sacrificial material of the template is insoluble; or, in the case in which the precursor is used in solution, the sacrificial material must be insoluble in the solvent.

It is also possible for the sacrificial material to be slightly soluble in the precursor (liquid) or in the solvent thereof (if used in solution). In this case, it is necessary for the solubility of the sacrificial material in the precursor or in the solvent to be sufficiently low as to make it possible for the template to remain continuous throughout the time necessary for solidification of the precursor, such that in no point the material of the matrix goes to block a channel or cavity desired in the channel network of the final device.

In turn, the material of the matrix (the choice of which depends on the choice of precursor) must be insoluble in the solvent of the sacrificial material, in case the removal thereof happens by chemical means, or unalterable at the melting temperature of the sacrificial material in the event of this being removed by heat treatment. In particular, if the method selected for removal of the sacrificial material is melting, the material of the matrix must have a melting temperature, and preferably also a $T_g$, higher than the melting temperature of the sacrificial material.

In case it is desired to increase the chemical incompatibility of the material of the template with that of the matrix, so as to improve the replicability of the geometry of said template in the channels of the final matrix, it is also possible—before pouring the precursor (or a solution thereof) into the mould—to cover the template with a suitable chemical agent; for example, if the material of the matrix consists of poly(ethylene glycol) (PEG) hydrogel, the surface of the template can be covered with a thin layer of a silicon oil.

Whether liquid or in solution, the precursor may be composed of monomers or oligomers of a polymer, which are made to polymerise in situ (for example, by triggering polymerisation with radical initiators, by irradiating with light of a suitable wavelength, normally within the UV range or, again, thermally). In general, the material of the matrix can be any reticulated or non-reticulated polymer, and more generally any material capable of solidifying starting out from a liquid precursor, provided that, once solid, it is compatible with removal of the sacrificial material.

Among the possible matrix materials, the preferred one for various applications is polydimethylsiloxane (PDMS) on account of the ease of its production and use, because it is transparent, gas-permeable and flexible.

Another material suited to production of the matrix of the device is polystyrene (PS), widely used in biomedical applications and cell culturing on account of the low cost of production, non-toxicity and excellent transparency.

In one variant of particular interest, the material of the matrix is produced from a solution containing species which polymerise to form hydrogels, yielding a final device the matrix of which contains high doses (normally of approximately 2% to 99% by weight) of water; a microfluidic device of this design is normally especially suitable for the production of scaffolds for use in implants in the human (or animal) body.

In particular, these materials consist of water-insoluble reticulated polymers which physically entrap elevated quantities of water, even up to 99% by weight; typical examples of polymers that are able to form hydrogels are the polyamidoamines and polyhydroxyethylmethacrylate (PHEMA). It is also possible to use soluble polymers which are insoluble once reticulated; examples of these polymers are poly(N-isopropylacrylamide) (PNIPAAM), polyethylene glycol (PEG), polycaprolactone (PCL), collagen, agarose, chitosan and alginate.

Typical sacrificial material/matrix material pairs in the case of removal of the former by melting are PMMA/PDMS and PS/epoxy resins; where removal of the sacrificial material is by solvent, typical pairs are PMMA-PDMS (solvents: acetone, acetic acid), PMMA-PHEMA (solvents: acetone, acetic acid), PVA-PHEMA (solvent: water), PVA-PDMS (solvent: water), PVA-PS (solvent: water), PVA-PEG (solvent: water), PS-collagen (solvent: acetone), PMMA-chitosan (solvent: acetone) and PMMA-PCL (solvent: acetone).

The precursor is then allowed to solidify, and the solid body obtained is removed from the mould.

Finally, the assembly consisting of the solid body thus obtained, still containing the template, is subjected to a treatment of selective removal of the latter. In case of removal by heat treatment, said assembly is brought to a temperature higher than the melting point of the sacrificial material but lower than that of the device body material (and preferably lower than the $T_g$ of the latter). Alternatively, said assembly is inserted into a vessel (commonly of dimensions greater than the mould in which it has been formed), into which a solvent of the sacrificial material is introduced, until total dissolution of the latter. In both cases, a solid body is obtained which contains a three-dimensional network of channels and other empty spaces, according to the desired design. FIGS. 1.f and 2.f show the two microfluidic devices obtained, 19 and 29, by the sequence of steps of the method in the case of use of the three-dimensional templates 15 and 25 respectively; the devices shown are transparent to make evident the three-dimensional network of internal channels.

In the case in which the surface of the sacrificial three-dimensional template had been covered (even only partially) with a functional material (for example metallic particles) before immersion in the liquid precursor, said functional material remains adherent or partially consolidated in the materials of the matrix during its formation; following dissolution and removal of the template, the functional material is thus transferred to the internal surface of the channels or of the other empty spaces of the device. Examples of materials which may be transferred in this way onto the internal surfaces of the channels are proteins and metallic nanoparticles.

The method of the present invention also allows production of vascularised scaffolds exhibiting better survival of the cells contained therein. Scaffolds of this type may also be used for numerous applications of cell culturing, for example for the production of biopharmaceuticals in vitro and/or for screening of pharmaceuticals or therapies in vitro, or for the production of implants and prostheses for surgical applications. In the case of surgical implants and prostheses, these scaffolds constitute a support, permanent or temporary, for colonisation by the cells of the body; in the case of permanent implants, colonisation of the surfaces of the scaffold permits the integration and compatibility with the tissues of the body whereas, in the case of temporary implants, the scaffolds must offer provisional support to the cells of the tissue, and then be degraded by the body fluids within times compatible with those of cell regrowth, or be metabolised by the same cells in the growth phase. As is known, these systems exhibit channellings, not necessarily ordered or of regular geometry, having the purpose of enabling the transportation of body fluids which carry oxygen and nutritive elements to the cells. One problem of vascularised systems of the known art is that the transportation of fluids within the materials of which said systems are comprised is difficult. The consequence is that, while the cells present on the surfaces of the scaffold, including those of the internal channels, have adequate survival times, cells more distant from said surfaces have survival times that are too short and do not allow rates of cell reproduction and thus of tissue regrowth compatible with the aims indicated above.

Patent application WO 2010/009320 A1, discussed previously, faces the problem and offers a means of forming scaffolds with principal vascularisations of relatively large cross-section, surrounded by a diffuse network of microchannels within the scaffolds; however, the solution proposed by this document has the disadvantages described above, that it is relatively complex to produce, and that it cannot be guaranteed that the filaments of sacrificial materials, destined to form the microchannels, do not collapse under the weight of the liquid precursor of the scaffold matrix.

The method of the present invention, in one variant, enables the problems of the prior art to be overcome.

According to this method, the process steps described above are repeated, with the sole difference that porogenic materials are introduced into the liquid precursor (or containing the precursors) of the scaffold matrix.

These porogenic materials can be powders of a sacrificial material, which may be the same or different from that used to form the template. Other porogenic materials which can be used are those which develop gas in solution (e.g. $NaHCO_3$), or surfactants or similar materials that give rise to emulsions or foams, with consequent solidification of the precursor in the form of a foam.

Further to the principal channels obtained by removal of the template, the scaffold matrix thus produced has a secondary apertures structure composed of interconnected pores. This secondary structure is filled with cells by means of injection into the matrix or seed via the channels. The cells homogenously colonise the scaffold thanks to the possibility of migrating via the interconnections between pores. These cells are preferably autologous, that is, harvested from the same individual in whom the scaffold or the tissue regrowing therefrom is to be implanted, thus avoiding problems of rejection. For producing the matrix, materials are preferably used which degrade completely once inserted into the body of the patient (human or animal), without generating inflammatory effects. Examples of these materials are PCL, collagen and chitosan.

In a variant of production of these devices, the cells may be inserted directly into the liquid precursor of a hydrogel before or during encapsulation of the template and of possible porogens; hydrogels containing living cells are designated in the field by the definition "cell-laden". The sacrificial material (of the template and of any porogen) is then removed with solvents compatible with the cells, in general saline solutions. In this case, a cell-loaded hydrogel with microfluidic channels and possibly porosity is obtained.

The invention will be further illustrated by means of the following examples.

The following materials were used when conducting the tests reported in the examples:

poly(methyl methacrylate) (PMMA), 445746-1 KG (Sigma-Aldrich)
polyvinyl alcohol (Mowiol), Mowiol 4-88 (Sigma-Aldrich)
polyvinyl alcohol (PVA), Mowiflex TC253 (Kuraray)
polydimethylsiloxane (PDMS), Sylgard 184 (Dow Corning)
2-hydroxyethyl methacrylate (HEMA), code 128635 (Sigma-Aldrich)
ethylene glycol dimethacrylate (EGDMA), code 335681 (Sigma-Aldrich)
N,N,N',N'-tetramethylethylenediamine (TEMED), code T22500 (Sigma-Aldrich)
ammonium persulphate (APS), code A3426 (Sigma-Aldrich)
ethanol, code 51976 (Sigma-Aldrich)
castor oil, code 259853 (Sigma-Aldrich)
polyethylene glycol diacrylate MW6000 (PEGDA), code 701963 (Sigma-Aldrich)
dimethylsulfoxide (DMSO), code 472301 (Sigma-Aldrich)
photoinitiator additive Irgacure 2959 (CIBA)
mould release product Nano HS (BPItech)
silicone spray ALS (AMSOIL)
sodium chloride, code 71376 (Sigma-Aldrich)
culture medium DMEM (Dulbecco's modified Eagle's medium), code D5546 (Sigma-Aldrich)
saline phosphate buffer (PBS), code P5493 (Sigma-Aldrich)
acryloil-polyethyleneglycol-RGDS (APEG-RGDS), synthesised as described in the article "Smooth muscle cell growth in photopolymerized hydrogels with cell adhesive and proteolytically degradable domains; the fourth of synthetic ECM analogs for tissue engineering", B. K. Mann et al, Biomaterials (2001) Vol. 22, pages 3045-51
LIVE/DEAD® Viability/Cytotoxicity Kit, for mammalian cells, code L-3224 (Invitrogen).

EXAMPLE 1

This example relates to the production of an elastomer-based device having 500-μm channels and internal micro-wells for biological applications, using the method with master described with reference to FIG. 1.

Template production: in an aluminum master (master 13, FIG. 1.*b*) pretreated with Nano HS and heated to 140° C., molten PVA is injected at 190° C. via the lateral aperture 14, until the internal spaces are completely filled. The master is then cooled to ambient temperature, the two component parts are separated and the PVA template 15 thus formed is removed mechanically.

Production of the PDMS-based matrix: the liquid PDMS precursor Sylgard 184 (13.5 g) and the relevant reticulating agent (1.5 g) (included in the sales pack of Sylgard 184) are introduced, in order, into a 250 ml beaker, and mixed by hand using a glass rod for approximately 1 minute. The mixture is then placed in a chamber at reduced pressure (10 mbar) for 60 minutes to eliminate the bubbles present in the liquid, after which the mixture is poured into the PMMA mould 16 containing the template 15; the template is suspended in the mould, not in contact with the cavity floor 17, by means of its two ends inserted into the grooves 18 and 18'. The mould is then sealed to prevent escape of liquid and reaction at ambient temperature is allowed to take place for 48 hours (alternatively, operation at 60° C. for 6 hours is possible). The mould is then opened and the block of solid PDMS is removed.

Template removal: the block of PDMS containing the template is immersed in bi-distilled water while maintaining the assembly under magnetic agitation for 24 hours at 90° C. In this way the template solubilises in water leaving no traces on the PDMS matrix. At the end of this procedure, the device 19 with channelings and micro-wells is ready for use.

EXAMPLE 2

This example relates to the production of an elastomer-based device having 500-μm channels and internal micro-wells for biological applications, and is a variant of example 1.

Template production: onto a microfabricated part of the type 10 shown in FIG. 1.*a*, positioned inside a mould and pretreated with Nano HS and heated to 50° C., an aqueous solution of Mowiol (50/50 by weight) heated to 70° C. is poured, depositing a film of approximately 1-3 mm over the whole surface of the mould (casting). The mould is then cooled to ambient temperature and the solvent is allowed to evaporate for 24 hours under a stream of air. By means of an etching process (using a cloth soaked in water and ethanol), the layer of Mowiol is brought into perfect alignment with the upper limit of the cavities resulting from the microfabrications. After placing the mould in a reduced-pressure chamber (10 mbar) 4 hours, the Mowiol template thus moulded is removed.

Production of the PDMS-based matrix: the liquid PDMS precursor Sylgard 184 (13.5 g) and the relevant reticulating agent (1.5 g) (included in the sales pack of Sylgard 184) are introduced, in order, into a 250 ml beaker, and mixed by hand using a glass rod for approximately 1 minute. The mixture is then placed in a reduced-pressure chamber (10 mbar) for 60 minutes to eliminate the bubbles present in the liquid, after which the mixture is poured into the PMMA mould 16 containing the sacrificial structure of Mowiol supported by the two parts B and B' in the grooves 18 and 18'. The mould is then sealed to prevent escape of liquid and reaction at ambient temperature is allowed to take place for 48 hours (alternatively, at 60° C. for 6 hours). The mould is then opened and the block of solid PDMS is removed.

Template removal: the block of PDMS containing the Mowiol template is immersed in bi-distilled water maintaining the assembly under magnetic agitation for 24 hours at 90° C., changing the solution every 8 hours. In this way the template solubilises in water leaving no traces on the PDMS matrix. At the end of this procedure, the device 19 with channelings and micro-wells is ready for use.

EXAMPLE 3

This example relates to the production of a hydrogel-based device having 500-μm channelings and internal micro-wells for biological applications.

Template production: procedure as in example 1, the only difference being that the master 13 is heated to 120° C., and, instead of PVA, molten PMMA is injected into the master at 170° C.

Production of the matrix based on poly(2-hydroxyethyl methacrylate) (PHEMA) hydrogel: HEMA (6.00 g, 46.1 mmol), water (3 ml), EGDMA (60.0 mg, 0.303 mmol) and TEMED (81.4 mg, 0.701 mmol) are introduced, in order, into a 50 ml flask, mixing for 30 sec with a magnet stirrer following addition of each component. An aqueous solution of 10% by weight of APS (75.0 μl, 0.0322 mmol) is then added, it is stirred by hand for 30 sec, then the mixture is poured into the PMMA mould (16) containing the sacrificial structure. The mould is then sealed to prevent evaporation of the liquid components and the mixture is allowed to react for 24 hours at ambient temperature. The mould is then dismantled, the moulded hydrogel containing the template is removed and immersed in an aqueous solution of ethanol (50% v/v, 30 ml), changing the solution every 4 hours three times over.

Removal of the sacrificial structure: the PHEMA hydrogel containing the PMMA sacrificial structure is immersed in acetone, with magnetic stirring for 48 hours at 50° C., changing the solution every 12 hours. In this way, the PMMA template solubilises leaving no traces on the hydrogel. Subsequently, the hydrogel is immersed in a solution of ethanol for 4 hours and then, for the same time, in an aqueous solution of ethanol (50% v/v, 30 ml), thereafter washing in bi-distilled water (50 ml) is performed, changing the solution every 4 hours three times over. At the end of this procedure, the device with channelling and micro-wells 19 is ready for use.

EXAMPLE 4

This example relates to the production of a hydrogel-based device having 500-μm channelings and internal micro-wells for biological applications, and is a variant of example 3.

Production of the sacrificial structure: the aluminum master of type 13 pretreated with Nano HS is left partially open and heated to 120° C. Into the space left between the two parts (10 and 12) of the mould, molten PMMA is injected at 170° C. Following this injection phase, the two parts of the mould are joined by means of a press using a compressive force of 10,000 kg. When the desired compressive force is reached, the maintenance phase starts, with controlled force of the final pressure until complete cooling of the mould. At the end of the described process the two parts making up the mould are separated and the PMMA template 15 formed is removed mechanically.

Production of the matrix based on poly(2-hydroxyethyl methacrylate) (PHEMA) hydrogel: HEMA (6.00 g, 46.1 mmol), water (3 ml), EGDMA (60.0 mg, 0.303 mmol) and TEMED (81.4 mg, 0.701 mmol) are introduced, in order, into a 50 ml flask, mixing for 30 sec with a magnet stirrer following addition of each component. An aqueous solution of 10% by weight of APS (75.0 μl, 0.0322 mmol) is then added, it is stirred by hand for 30 sec, then the mixture is poured into the PMMA mould (16) containing the template. The mould is sealed to prevent evaporation of the liquid components and the mixture is allowed to react for 24 hours at ambient temperature. The mould is then dismantled, the moulded hydrogel containing the sacrificial structure is removed and immersed in an aqueous solution of ethanol (50% v/v, 30 ml), changing the solution every 4 hours three times over.

Template removal: the PHEMA hydrogel containing the PMMA sacrificial structure is immersed in acetone, with magnetic stirring for 48 hours at 50° C., changing the solution every 12 hours. In this way, the PMMA template solubilises leaving no traces on the hydrogel. Subsequently, the hydrogel is immersed in a solution of ethanol for 4 hours and then in an aqueous solution of ethanol (50%, v/v, 30 ml) for the same time, thereafter washing in bi-distilled water (50 ml) is performed, changing the solution every 4 hours three times over. At the end of this procedure, the device 19 with channelings and micro-wells is ready for use.

EXAMPLE 5

This example relates to the production of a porous and vascularised scaffold based on hydrogel, for applications in tissue engineering.

Production of the template of minimum size 200 in an aluminum master of type 23, shown in FIG. 2._b_, pretreated with Nano HS and heated to 120° C., molten PMMA is injected at 170° C. via the lateral aperture 24, until the internal spaces are completely filled. The master is then cooled to ambient temperature, the two component parts are separated and the PMMA structure thus moulded is removed mechanically.

Production of the matrix based on polyethylene glycol (PEG) hydrogel: PEGDA 6000 (6,500 mg, 1.08 mmol), a saturated solution of sodium chloride (7.2 ml), a solution of Irgacure 2959 in ethanol (450 μl, 100 mg Irgacure/ml of ethanol), sodium chloride powder with porogenic function (3,500 mg, 59.89 mmol) are introduced, in order, into a 50 ml flask and mixed with a magnetic stirrer for 10 minutes. The mixture is poured into the PMMA mould 26 containing the PMMA template (FIG. 2.*e*), the mould is then sealed to prevent evaporation of the liquid components and the mixture is allowed to react for 10 minutes under UV irradiation (365 nm, 120 W mercury vapour bulb, distance 20 cm) at ambient temperature. The mould is then dismantled, the moulded hydrogel containing the template is removed and immersed in an aqueous solution of ethanol (50% v/v, 30 ml), changing the solution every 4 hours three times over.

Removal of the template and porogen: the hydrogel containing the PMMA sacrificial structure is immersed in acetone, with magnetic stirring for 48 hours at 50° C., changing the solution every 12 hours. In this way, the PMMA sacrificial structure solubilises leaving no traces on the hydrogel.

Subsequently, the hydrogel is immersed in a solution of ethanol for 4 hours and then in an aqueous solution of ethanol (50%, v/v, 30 ml) for the same time, thereafter washing in bi-distilled water (50 ml) is performed at 50° C. for 72 hours, changing the solution every 12 hours six times over. Washing in water allows the salt particles included in the matrix to solubilise, leaving the porous structure in their place. Finally, the hydrogel is immersed first in a saline solution (PBS, 30 ml) for 4 hours and then in the culture medium (DMEM 1640, 30 ml) for 4 hours. At the end of this procedure, the porous and vascularised scaffold 29 is ready for use with the cells.

EXAMPLE 6

This example relates to the production of a vascularised scaffold based on cell-laden polyethylene glycol (PEG) hydrogel for tissue engineering applications.

Template production: in an aluminum master of type 23, shown in FIG. 2.*b*, pretreated with Nano HS and heated to 140° C., molten PVA is injected at 190° C. via the lateral aperture 24, until the internal spaces are completely filled. The master is then cooled to ambient temperature, the two parts making up the mould are separated and the PVA template thus formed is removed mechanically. In this case the surface of the template is treated with Silicon Spray ALS to render it hydrophobic.

Production of the matrix based on hydrogel of polyethylene glycol (PEG): PEGDA (1,500 mg, 0.250 mmol), APEG-RGDS (164 mg, 0.0450 mmol), a solution of PBS (13.5 ml, pH 7.4) with 3T3 fibroblasts in suspension ($10^6$ cells/ml), a solution of Irgacure 2959 in DMSO (300 µl, 200 mg Irgacure/ml of DMSO) are introduced, in order, in a 50 ml flask, and mixed with a magnetic stirrer for 2 min. The mixture is poured into the PMMA mould 26 containing the PVA template (FIG. 2.*e*). The mould is sealed to prevent evaporation of the liquid components and the mixture is allowed to react for 3 minutes under UV irradiation (365 nm, 120 W mercury vapour bulb, distance 20 cm) at ambient temperature. The high concentration of solutes in the aqueous mixture and the hydrophobic coating do not allow the PVA to dissolve during polymerisation of the hydrogel-based matrix. The mould is then dismantled and the moulded hydrogel containing the template is removed.

Template removal: the hydrogel is immersed in a saline solution (PBS, 30 ml) for 2 hours, and then in the culture medium (DMEM 1640, 30 ml) for 8 hours, allowing the complete solubilisation of the PVA template. At the end of this procedure, the porous and vascularised scaffold 29 with pre-loaded cells is ready for use.

EXAMPLE 7

Example 2 is repeated, using a solution of castor oil in ethanol (3 ml, 200 castor oil mg/ml) in place of Nano HS for pretreating the mould; the results obtained are the same as those for example 2.

EXAMPLE 8

This example demonstrates the capacity of a vascularised scaffold of the invention to keep alive the cells contained therein.

The scaffolds produced in example 6 is connected to a syringe pump and fed for three days with DMEM culture medium for cells at a velocity of 10 microliters per minute. During the test, the scaffold is kept in an incubator at 37° C. and 5% $CO_2$, inside a sterilised container. At the end of the test, a slice of scaffold 1 mm thick and perpendicular to the channel to which the syringe was connected is cut using a surgical scalpel; the slice is subjected to a fluorescence test which detects the live cells, by means of the LIVE/DEAD method using the LIVE/DEAD® Viability/Cytotoxicity Kit. The test results are shown in the upper part of FIG. 3, which shows the scaffold at the start (image 3.*a*) and at the end (image 3.*b*) of the same test, after 72 hours; the circular broken line indicates the position of the microfluidic channel.

EXAMPLE 9

Comparative

The test in example 8 is repeated with a scaffold not of the invention, in particular produced by the same method as in example 6, except for the insertion of the sacrificial template, and thus without the microfluidic channelling. The bottom of FIG. 3 shows the scaffold at the start (image 3.*c*) and at the end (image 3.*d*) of this test.

As can be noted from comparison of the images 3.*b* and 3.*d*, after three days of testing in the case of the scaffold of the invention, the number of live cells is much greater than in the case without channelling; it is believed that the much greater capacity of the scaffold of the invention to keep the cells contained in its matrix alive is due to the much greater possibility of exchange of material with the outside environment, in particular for bringing nutrients and oxygen to the cells and for eliminating the waste products generated by the cells themselves.

The invention claimed is:

1. A method for producing a monolithic three-dimensional microfluidic device, comprising the following steps:
   producing, with a sacrificial material, a three-dimensional template of stable form, consisting of a part corresponding to channelling of the microfluidic device, and one or more parts not corresponding to said channelling;
   positioning said three-dimensional template into a mould by suspending it from at least one of said parts not corresponding to said channelling;
   coating said three-dimensional template, leaving out said parts not corresponding to said channelling, with a precursor, liquid or in solution, of a solid matrix, said precursor being able to solidify by chemical reaction or physical transformation forming a matrix making up a body of the monolithic three-dimensional microfluidic device;

causing solidification of said precursor;

selectively removing the sacrificial material by a heat treatment and/or by dissolution with a solvent thereof;

wherein into the liquid precursor or into the solution of the solid matrix precursor, powders of a porogenic sacrificial material are introduced, which can be equal or different from the sacrificial material used to form the three-dimensional template, and a resulting matrix material is porous, whereby further to said channelling of the microfluidic device obtained by removal of the three-dimensional template, the matrix thus produced has secondary apertures composed of interconnected pores.

2. A method according to claim 1, wherein the three-dimensional template is made up of a union of two or more separate parts.

3. A method according to claim 1, wherein the three-dimensional template is obtained by deformation of a structure made of a sacrificial material.

4. A method according to claim 1, wherein before the step of coating the three-dimensional template in the mould with said precursor liquid or in solution, a surface of said template is completely or partially coated with a layer of a material differing from the sacrificial material and from the precursor which, following dissolution of the sacrificial material, remains adherent to an internal surface of the matrix of the monolithic three-dimensional microfluidic device.

5. A method according to claim 4, wherein said material differing from the sacrificial material and from the precursor is insoluble in the precursor and/or in its solvent.

6. A method according to claim 1, wherein said sacrificial material is a wax or a thermoplastic polymer selected from poly(methyl methacrylate) (PMMA), polyvinyl alcohol (PVA), polycarbonate (PC) and polystyrene (PS).

7. A method according to claim h wherein the matrix material forming the body of the final device is selected from epoxy resins, polydimethylsiloxane (PDMS), polyurethane (PU), polyamidoamines (PAA), poly(hydroxyethyl methacrylate) (PHEMA), poly-N-isopropylacryamide (PNIPAAM), polyethylene glycol (PEG), polycaprolactone (PCL), polylactic acid (PLA), poly(lactic-co-glycolic) acid (PLGA), poly(vinyl alcohol) (PVA) hydrogel, collagen, agarose, chitosan, alginate, fibrinogen, hyaluronic acid, gelatin and dextran.

8. A method according to claim 1, wherein the sacrificial material is removed by dissolution with a solvent, and the sacrificial material and the matrix material of the body of the device are selected from PMMA-PDMS (solvent: acetone), PMMA-PHEMA (solvent: acetone), PVA-PHEMA (solvent: water), PVA-PDMS (solvent: water) and PVA-PEG (solvent: water).

9. A method according to claim 1 for producing vascularized supports for cell culture applications wherein the matrix of the device is made of a biocompatible and/or biodegradable material.

10. A method according to claim 1, wherein the secondary apertures are filled with cells by injection into the matrix or seed via the channels whereby said cells homogenously colonise and are capable of migration via the interconnections between pores.

11. A method according to claim 1, wherein said porogenic material, different from that of the three-dimensional template, is selected from materials evolving gas in solution, solvents, oils, surfactants or foaming agents.

12. A method according to claim 2, wherein the three-dimensional template is obtained by deformation of a structure made of a sacrificial material.

13. A method according to claim 10, wherein the cells filling said secondary apertures are autologous.

14. A method according to claim 1, wherein said matrix material degrades completely once inserted into a body of a patient without generating inflammatory effects.

15. A method according to claim 1, wherein said matrix material is selected from the group consisting of polycaprolactone (PCL), collagen and chitosan.

16. A method according to claim 10, wherein said cells are inserted into the matrix by charging them into the liquid precursor or into the precursor solution from which the matrix is produced.

* * * * *